US008927734B1

(12) United States Patent  
Caruana et al.

(10) Patent No.: US 8,927,734 B1
(45) Date of Patent: Jan. 6, 2015

(54) SINGLE REACTION VESSEL PROCESS FOR SYNTHESIS OF SALTS OF DNP

(71) Applicants: Patrick Caruana, Waldorf, MD (US); Bradley Sleadd, La Plata, MD (US); John Fronabarger, Sun Lakes, AZ (US); Michael D. Williams, Chandler, AZ (US)

(72) Inventors: Patrick Caruana, Waldorf, MD (US); Bradley Sleadd, La Plata, MD (US); John Fronabarger, Sun Lakes, AZ (US); Michael D. Williams, Chandler, AZ (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/986,710

(22) Filed: May 1, 2013

(51) Int. Cl.
*C07D 271/12* (2006.01)

(52) U.S. Cl.
CPC .................... *C07D 271/12* (2013.01)
USPC ........................ 548/126; 149/109.6

(58) Field of Classification Search
USPC ....................................... 149/109.6
See application file for complete search history.

(56) References Cited

U.S. PATENT DOCUMENTS

| 3,006,957 | A | 10/1961 | Murray et al. |
| 5,256,220 | A | 10/1993 | Baroody et al. |
| 5,993,577 | A | 11/1999 | Erickson et al. |
| 8,062,443 | B2 | 11/2011 | Fronabarger et al. |
| 8,216,401 | B1 | 7/2012 | Fronabarger et al. |
| 8,277,585 | B1 | 10/2012 | Yalamanchili et al. |
| 2007/0258147 | A1 | 11/2007 | Van der Boom et al. |
| 2009/0223401 | A1 | 9/2009 | Fronabarger et al. |
| 2011/0105800 | A1 | 5/2011 | Fronabarger et al. |

FOREIGN PATENT DOCUMENTS

EP 2496551 9/2012

OTHER PUBLICATIONS

Fronabarger et al. "KDNP—A Lead Free Replacement for Lead Styphnate" Propellants, Explosives, Pyrotechnics (2011), 36(5), 459-470.*
Prof Dr. Thomas M. Klapotke, Perchlorate and Halogen-Free High Energy Dense Oxidizers (HEDO), Jun. 2011, Ludwig-Maximilian University Munich.
John Fronabarger, Michael Williams, Environmentally Acceptable Alternatives to Existing Primary Explosives, May 2010, NAVSEA Indian Head, MD.

* cited by examiner

*Primary Examiner* — Samantha Shterengarts
*Assistant Examiner* — Amanda L Aguirre
(74) *Attorney, Agent, or Firm* — Fredric Zimmerman

(57) ABSTRACT

A batch reactor process for the synthesis of potassium 5,7-dinitro-[2,1,3]-benzoxadiazol-4-olate-3-oxide (KDNP) from 3-bromo-2,4,6-trinitroanisole (ETNA) includes adding BTNA to a reaction vessel containing potassium azide ($KN_3$) and water ($H_2O$). The resulting mixture is heated to 90° C. followed by cooling to room temperature and agitating the final solution. The precipitate KDNP product is recovered by filtration.

20 Claims, 1 Drawing Sheet

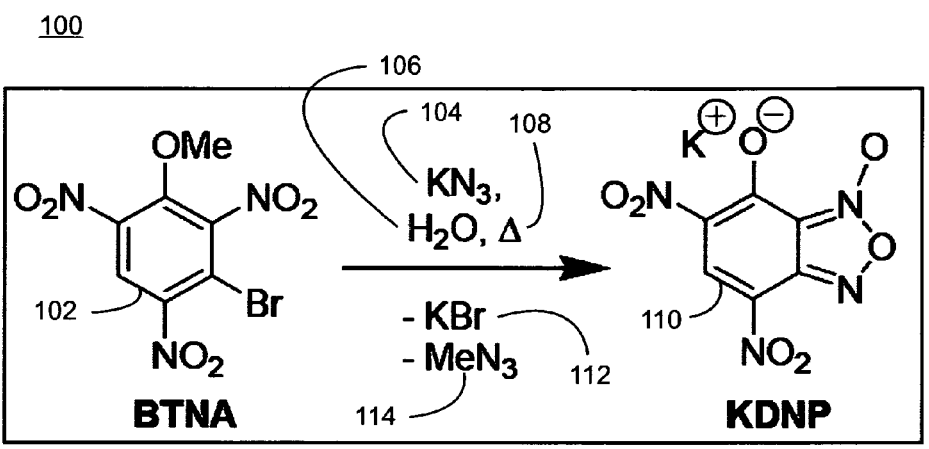

SINGLE REACTION VESSEL PROCESS FOR SYNTHESIS OF SALTS OF DNP

STATEMENT OF GOVERNMENT INTEREST

The invention described herein may be manufactured and used by or for the Government of the United States of America for Governmental purposes without the payment of any royalties thereon or therefore.

BACKGROUND OF INVENTION

1) Field of the Invention

The present invention is directed to energetic materials and in particular to a method for the synthesis of KDNP, a lead-free replacement to lead styphnate.

2) Description of Prior Art

There is growing interest in the manufacture and scale-up of alternative replacements to heavy metal-containing energetic materials based on regulatory changes and clean-up costs associated with heavy metal waste. The compound, potassium 5,7-dinitro-[2,1,3]-benzoxadiazol-4-olate-3-oxide (KDNP), has been qualified by the Navy as a primary explosive and is being developed as a suitable replacement for lead styphnate.

Previous attempts to synthesize KDNP, however, have resulted in bench scale quantities of the compound that required multiple steps for the synthesis of KDNP. For example, the method reported by Fronabarger et al. in U.S. Pat. No. 8,062,443 and "KDNP—A Lead Free Replacement for Lead Styphnate", Propellants Explos. Pyrotech, 36, pages 459-470, 2011, requires several laboratory operations to convert BTNA to KDNP, including the use of multiple solvents and separation steps in the preparation of KDNP. Therefore, an efficient and commercially viable process is desired for the synthesis and production of larger quantities of KDNP using a minimal number of processing steps.

SUMMARY OF THE INVENTION

Exemplary embodiments of systems and methods in accordance with the present invention provide a method for the synthesis of salts of 5,7-dinitro-[2,1,3]-benzoxadiazol-4-olate-3-oxide (DNP) and in particular potassium DNP (KDNP) from 3-bromo-2,4,6-trinitroanisole (BTNA) using a single reaction vessel process as well as other salts of DNP. A process for synthesizing KDNP from BTNA is utilized such that simple and efficient production of KDNP can be achieved in commercially viable quantities from a single batch reactor process having a minimal number of steps. The process includes adding $KN_3$ to a reactor vessel containing BTNA and water ($H_2O$), heating the mixture at about 90° C. for up to 7 hours, cooling the mixture to about room temperature (about 20° C. to about 25° C.), mixing the solution for up to about 12 hours, and recovering the resulting KDNP precipitate through filtration. A continuously aqueous solution is maintained throughout the process such that KDNP is retained in the liquid as a precipitate upon completion of the reaction and is directly filtered from the solution.

BRIEF DESCRIPTION OF THE DRAWINGS

It will be understood that many additional changes in details, materials, steps, and arrangements of parts which have been described herein and illustrated in order to explain the nature of the invention, may be made by those skilled in the art within the principle and scope of the invention as expressed in the appended claims.

FIG. 1 is a chemical formula indicating the process of KDNP synthesis.

DETAILED DESCRIPTION OF THE INVENTION

Referring to FIG. 1, an exemplary embodiment for the synthesis of a salt of 5,7-dinitro-[2,1,3]-benzoxadiazol-4-olate-3-oxide (DNP) 100 and in particular potassium DNP (KDNP) in accordance with the present invention is illustrated. The synthesis is achieved in a single reaction vessel using a process that in addition to generating about 10 mg to about 1 gram of KDNP can be scaled to commercial production of KDNP in amounts of from about 1 gram to about 1 Kg or more. Large scale commercialization is facilitated by the single reaction vessel batch process as well as the use of a minimum number of reaction steps and the elimination of non-aqueous solvents.

A quantity of 3-bromo-2,4,6-trinitroanisole (BTNA) 102 is added to the single reaction vessel along with an azide and a solvent. Suitable azides include the alkali metal azides, for example, sodium and potassium. Other azides include organic azide salts. The use of other azide salts in the process would lead to other salts of 5,7-dinitro-[2,1,3]-benzoxadiazol-4-olate-3-oxide. Systems and methods in accordance with the present invention can be used to produce any desired salt of DNP from an azide in a single reaction vessel at desired commercially viable quantities. In an exemplary embodiment, the azide is potassium azide ($KN_3$) 104.

The resulting solution is, in an exemplary embodiment, an aqueous solution, and the solvent is water ($H_2O$) 106. However, a person of ordinary skill in the relevant art would understand that a variety of high-boiling organic solvents may also be used. The reaction components may be combined in any order or sequence suitable to effectuate the reaction of BTNA with the azide in the solvent. Preferably, the azide is added to a reaction vessel containing a pre-mixed starter slurry of the solvent and BTNA. In one embodiment, the starter slurry is pre-mixed at a ratio of BTNA to solvent, e.g., water, of from about 1.15 g of BTNA to from about 3.4 to about 10 mL of solvent. In one embodiment, the BTNA and azide, i.e., $KN_3$, are added to the single reaction vessel at a mol ratio BTNA:Azide of from about 1:1 to about 1:2.1.

The single reaction vessel containing the BTNA, azide and solvent mixture is heated 108 to a predetermined temperature and maintained at that predetermined temperature for a given period of time in order to react the ETNA, azide and solvent. Suitable methods for heating include using a water bath in order to provide even heating and to maintain a consistent temperature. In one embodiment, the predetermined temperature is at least about 90° C. This temperature is maintained for up to about 7 hours, preferably up to about 3 hours.

Following the given period of time, the heated and reacted mixture of BTNA, azide and solvent is cooled. Active cooling, e.g., in an ice bath or cool water bath, can be used, or the single reaction vessel is allowed to cool to room temperature passively overnight. In one embodiment, the single reaction vessel and the reacted mixture of BTNA, azide and solvent is cooled to a range of about 20° C. to about 25° C. over a period of time of about 12 hours.

The reacted and cooled mixture of BTNA, azide and solvent is agitated, e.g., mechanically mixed or stirred, in the single reaction vessel for a predetermined period of time. In one embodiment, the predetermined period of time is up to about 3 hours.

The resulting salt of DNP, e.g., KDNP, 110 is recovered from the single reaction vessel as a precipitate, e.g., a light brown solid. Preferably, the KDNP precipitate is recovered by filtration. As the synthesis is conducted in a continuously aqueous system, a facile recovery step of KDNP by filtration of the precipitate from the solution can be used. This is in contrast to past attempts which required an evaporation step of the solution to dryness followed by a re-dissolving step before KDNP could be synthesized and ultimately recovered.

In addition to the KDNP, the reaction generates potassium bromide (KBr) 112, when potassium azide is used, and potentially methyl azide ($CH_3N_3$) 114 as by-products. The KBr remains in the aqueous solution during filtration. The $CH_3N_3$ is a gas that bubbles out of the single reaction vessel.

Reaction conditions, for example, the time for each step as well as the type and speed of mixing, can be varied to affect KDNP precipitate crystal formation. Discrete needles can be formed with a length of about 304 µm and a width of about 29 µm. A faster crystallization process yields agglomerates of rods, where each rod has a width of about 43 µm and a length of from about 61 µm to about 131 µm. In one embodiment, at least one crystal habit modifier can be added to the single reaction vessel in order to influence crystal morphology and crystal size of the KDNP. Suitable crystal habit modifiers include, but are not limited to, TWEEN 60® (polyethylene glycol sorbitan monostearate), methylcellulose and hydroxypropyl-methylcellulose. In another embodiment, changes to cooling rates and reaction concentration can influence crystal morphology and size. Alternatively, a separate recrystallization step using organic solvents may afford control of crystal morphology.

Systems and methods in accordance with the present invention provide the benefit of using a single reaction vessel with a reduced number of steps to produce KDNP from BTNA. The method can be scaled to larger reaction vessels to rapidly produce greater quantities of KDNP in a single batch process. Further, retaining KDNP product in the liquid phase is a desirable improvement over past attempts since the compound can be directly filtered from the solution. Therefore, the present invention is a suitable replacement for known methods to synthesize KDNP and can be used in commercial processes for large scale production of the compound.

In one exemplary embodiment for the synthesis of KDNP in accordance with the present invention, a round-bottomed flask, i.e., the single reaction vessel, was charged with a magnetic stir bar, BTNA (1.15 g, 3.57 mmol) and water (3.4 mL), and the resulting slurry was stirred vigorously using a heat/magnetic stir plate. To this slurry was added $KN_3$ (0.61 g, 7.50 mmol, 2.1 equiv), and the resulting mixture was heated to 90° C. in a water bath for 3 hours. Upon cooling to room temperature, a precipitate formed, and the mixture was allowed to stir at room temperature overnight. The product was filtered, washed with ice-chilled water (3×), and air-dried to afford KDNP (0.77 g) as a brownish orange solid. $^1H$ and $^{13}C$ NMR and DSC data matched reported values for KDNP.

While it is apparent that the illustrative embodiments of the invention disclosed herein fulfill the objectives of the present invention, it is appreciated that numerous modifications and other embodiments may be devised by those skilled in the art. Additionally, feature(s) and/or element(s) from any embodiment may be used singly or in combination with other embodiment(s). Therefore, it will be understood that the appended claims are intended to cover all such modifications and embodiments, which would come within the spirit and scope of the present invention.

What is claimed is:

1. A method for synthesizing potassium 5,7-dinitro-[2,1,3]-benzoxadiazol-4-olate-3-oxide (KDNP), comprising:
    combining 3-bromo-2,4,6-trinitroanisole (BTNA), potassium azide, and a solvent in a single reaction vessel;
    heating the single reaction vessel for a predetermined amount of time,
    cooling the single reaction vessel and the reacted combined BTNA, azide and solvent to room temperature;
    agitating the reacted combined BTNA, azide and solvent for a predetermined period of time; and
    recovering KDNP from the mixed reacted BTNA, azide and solvent as a precipitate.

2. The method of claim 1, wherein the solvent comprises one of a high-boiling organic solvent and water.

3. The method of claim 1, wherein said heating the single reaction vessel further comprises heating the single reaction vessel to a temperature of at least about 90° C.

4. The method of claim 1, wherein the method further comprises heating the single reaction vessel for a period of time of up to about 7 hours.

5. The method of claim 1, wherein the predetermined period of time comprises up to about 3 hours.

6. The method of claim 1, wherein recovering KDNP further comprises using filtration to recover the KDNP.

7. The method of claim 1, wherein the method further comprises adding at least one crystal habit modifier to the single reaction vessel to influence crystal morphology and crystal size of KDNP precipitate.

8. The method of claim 7, wherein the crystal habit modifier is selected from polyethylene glycol sorbitan monostearate, methylcellulose and hydroxypropyl-methylcellulose.

9. The method of claim 1, wherein said recovering KDNP further comprises recovering from about 1 gram to about 1 kilogram of KDNP.

10. The method of claim 1, wherein the Mol ratio of BTNA to azide in the single reaction vessel is from about 1:1 to about 1:2.1.

11. The method of claim 1, wherein the BTNA and solvent are combined in the single reaction vessel at a ratio of BTNA to solvent of from about 1.15 g of BTNA to from about 3.4 to about 10 mL of solvent.

12. A method for synthesizing salts of 5,7-dinitro-[2,1,3]-benzoxadiazol-4-olate-3-oxide (DNP), the method comprising:
    combining 3-bromo-2,4,6-trinitroanisole (BTNA), an azide and a solvent in a single reaction vessel;
    heating the single reaction vessel for a predetermined amount of time;
    cooling the single reaction vessel and the reacted combined BTNA, azide and solvent to room temperature;
    agitating the reacted combined BTNA, azide and solvent for a predetermined period of time; and
    recovering a salt of DNP from the mixed reacted BTNA, azide and solvent as a precipitate.

13. The method of claim 12, wherein the azide comprises an alkali metal azide.

14. The method of claim 13, wherein the alkali metal azide comprises sodium azide.

15. The method of claim 12, wherein the solvent comprises one of a high-boiling organic solvent and water.

16. The method of claim 12, wherein said recovering the salt of DNP further comprises using filtration to recover the salt to DNP.

17. The method of claim 12, wherein the method further comprises adding at least one crystal habit modifier is selected from polyethylene glycol sorbitan monostearate, methylcellulose and hydroxypropyl-methylcellulose to the single reaction vessel to influence crystal morphology and crystal size of DNP precipitate.

18. The method of claim 12, wherein said recovering the salt of DNP further comprises recovering from about 1 gram to about 1 kilogram of the salt of DNP.

19. The method of claim 12, wherein the Mol ratio of BTNA to azide in the single reaction vessel is from about 1:1 to about 1:2.1.

20. The method of claim 12, wherein the BTNA and solvent are combined in the single reaction vessel at a ratio of BTNA to solvent of from about 1.15 g of BTNA to from about 3.4 to about 10 mL of solvent.

\* \* \* \* \*